(12) United States Patent
Cho et al.

(10) Patent No.: US 8,131,347 B2
(45) Date of Patent: Mar. 6, 2012

(54) OPTICAL APPARATUS FOR MEASURING BIO-INFORMATION

(75) Inventors: Jae-Geol Cho, Yongin-si (KR); Jung-Taek Oh, Yongin-si (KR)

(73) Assignee: Samsung Electronics Co., Ltd., Maetan-Dong, Yeongtong-Gu, Suwon-Si, Gyeonggi-Do (KR)

( * ) Notice: Subject to any disclaimer, the term of this patent is extended or adjusted under 35 U.S.C. 154(b) by 732 days.

(21) Appl. No.: 12/148,202

(22) Filed: Apr. 17, 2008

(65) Prior Publication Data
US 2009/0024041 A1    Jan. 22, 2009

(30) Foreign Application Priority Data
Jul. 19, 2007  (KR) .................. 10-2007-0072233

(51) Int. Cl.
*A61B 6/00* (2006.01)

(52) U.S. Cl. ....................................... 600/473; 600/476
(58) Field of Classification Search .................. 600/473, 600/475–477; 606/9, 17
See application file for complete search history.

(56) References Cited

U.S. PATENT DOCUMENTS

| | | | |
|---|---|---|---|
| 4,633,087 A | 12/1986 | Rosenthal et al. | 250/341 |
| 4,850,365 A | 7/1989 | Rosenthal | 128/664 |
| 5,149,321 A * | 9/1992 | Klatz et al. | 604/500 |
| 5,419,321 A * | 5/1995 | Evans | 600/407 |
| 5,676,140 A * | 10/1997 | Ukawa et al. | 600/311 |
| 5,775,791 A | 7/1998 | Yoshikawa et al. | 362/31 |
| 6,070,092 A * | 5/2000 | Kazama et al. | 600/310 |
| 7,172,560 B2 | 2/2007 | Uchida et al. | 600/587 |
| 7,860,547 B2 * | 12/2010 | Kondoh et al. | 600/407 |
| 2002/0084417 A1 * | 7/2002 | Khalil et al. | 250/341.8 |
| 2005/0107707 A1 * | 5/2005 | Kondoh et al. | 600/473 |
| 2005/0168742 A1 | 8/2005 | Jung et al. | |
| 2006/0056661 A1 | 3/2006 | Einighammer et al. | |

FOREIGN PATENT DOCUMENTS

| | | |
|---|---|---|
| EP | 0 516 251 | 12/1992 |
| EP | 1 627 599 A2 | 2/2006 |
| JP | 2007-7267 | 1/2007 |
| KR | 2003-81369 | 10/2003 |
| KR | 2004-95489 | 11/2004 |
| WO | WO 96/27325 | 9/1996 |

\* cited by examiner

OTHER PUBLICATIONS

Feather, J.W., et al.; "A Portable Reflectometer for the Rapid Quantification of Cutaneous Haemoglobin and Melanin;" Physics in Medicine & Biology; Vo.l. 33, No. 6; Jun. 1, 1988; XP20023349.

*Primary Examiner* — Ruth S Smith
(74) *Attorney, Agent, or Firm* — Cha & Reiter, LLC

(57) ABSTRACT

Disclosed is an apparatus for measuring bio-information of a user. The apparatus includes an input device for receiving basic bio-information of the user, a first light source radiating a first light having a first wavelength on the surface of the skin, a second light source radiating a second light having a second wavelength on the surface of the skin, a third light source arranged so as to be placed in a more distant position from a photo detector than the first and the second light sources, said third light source radiating a third light having a third wavelength on the surface of the skin, the photo detector for detecting a first, second and third detection lights transmitted through the surface of the skin and converting said first, second and third detection light into electrical signals, said first, second and third detection light corresponding to said first, second and third wavelengths and a control unit for enabling the first, second and third light sources to be driven in a known order and for producing bio-information of the user on the basis of the inputted basic bio-information and intensities of the first, second and third detection lights.

13 Claims, 16 Drawing Sheets

OPTICAL APPARATUS FOR MEASURING BIO-INFORMATION

CLAIM OF PRIORITY

This application claims the benefit of the earlier filing date, pursuant to 35 U.S.C. §119(a), to that patent application entitled "Apparatus for Measuring Bio-information" filed in the Korean Intellectual Property Office on Jul. 19, 2007 and assigned Serial No. 2007-72233, the contents of which are incorporated herein by reference.

BACKGROUND OF THE INVENTION

1. Field of the Invention

The present invention relates to an apparatus and a method for measuring bio-information, and more particularly to an apparatus and a method for measuring information about the skin and subcutaneous fat by using light.

2. Description of the Related Art

Various methods for measuring body fat or the thickness of subcutaneous fat have been known to the general public. Methods for measuring the thickness of subcutaneous fat include a method for direct measurement using calipers, a method using ultrasonic waves, a method using Computerized Tomography (CT), Magnetic Resonance Imaging (MRI), and the like. The method for directly measuring the thickness of subcutaneous fat using calipers is inaccurate and inconvenient, and causes pain. The method for measuring the thickness of subcutaneous fat by using ultrasonic waves, or CT, or MRI require expensive equipment and experts. Also, since it is inconvenient to measure the thickness of subcutaneous fat because of the need for devices for implementing the previously described methods, research on measurement methods using light have been performed.

One method for measuring body fat or the thickness of subcutaneous fat by using light corresponds to illuminating light onto the surface of the skin of a living body, and then detecting light radiating from the surface of the skin due to multiple scattering and converting the detected light to an electrical signal. This method has advantages in that it is non-invasive, and has a short measurement time. Also, since an apparatus for implementing this method has a small size, the apparatus has an advantage that it can measure the thickness of subcutaneous fat on occasion.

FIG. 1 is a view illustrating an apparatus for measuring the thickness of subcutaneous fat according to the prior art. Biological tissue 130 has a structure in which respective layers corresponding to muscle 132, subcutaneous fat 134, and skin 136 having a thickness of 0.5 to 4 mm, are laminated in that order, and the skin 136 can be subdivided into a horny layer, the outer skin, and the true skin. The above apparatus 100 includes a Light Emitting Diode (LED) 110 and a Photo-Diode or PhotoDetector (PD) 120. The LED 110 and the PD 120 are separate from each other, and are arranged on the surface of the skin 136. If the LED 110 irradiates light having a wavelength in the band of near infrared on the surface of the skin 136, some light travels in a direction from the surface of the skin 136 to the muscle 132, some of the light is directed to the surface of the skin 136 due to multiple scattering. Most of the light is absorbed by the muscle 132. The PD 120 detects light radiating from the surface of the skin 136 and converts it to an electrical signal.

FIG. 2 is a graph illustrating a change in the output of the PD 120 as a function of the thickness of the subcutaneous fat 134 according to separation distances from the LED 110. The X axis represents the thickness of the subcutaneous fat 134 in millimeters (mm), and the Y axis represents the output voltage of the PD 120 in Volts (V). Herein, an 'SD' represents a Separation Distance between the LED 110 and the PD 120. FIG. 2 depicts output curves corresponding to cases where SDs equal 5 mm (expressed in a solid line including small squares), 10 mm (expressed in a solid line including small circles), and 20 mm (expressed in a solid line including small triangles), respectively. To examine the output curve relevant to each SD, it can be recognized that the thicker the subcutaneous fat 134 the more an output of the PD 120 increases toward becoming saturated. Also, it can be determined that the more distant the SD becomes, the wider the range of the thickness of the subcutaneous fat 134 that can be measured.

U.S. Pat. No. 4,850,365, entitled "Near Infrared Apparatus and Method for Determining Percent Fat in a Body", invented by Rosenthal et al., discloses technology in which light having a single wavelength is irradiated on the surface of the skin, and then, percent body fat is measured by detecting light radiating from the surface of the skin due to multiple scattering within the subcutaneous fat layer.

U.S. Pat. No. 4,633,087, entitled "Near Infrared Apparatus for Measurement of Organic Constituents of Material", invented by Rosenthal et al., discloses technology in which multiple rays of light having wavelengths different from one another are irradiated on the surface of the skin, and then, percent body fat is measured by detecting rays of light radiating from the surface of the skin due to multiple scattering within the subcutaneous fat layer.

However, since not only the thickness of subcutaneous fat but also the color and the thickness of the skin affects the output of the PD, the prior technologies of bio-information measurement have problems in that an error in percent body fat caused by the color and the thickness of the skin, or an error in the thickness of subcutaneous fat cannot be effectively corrected.

SUMMARY OF THE INVENTION

The present invention provides an apparatus for measuring bio-information, which can measure bio-information more accurately by using basic bio-information, which is input by a user.

In accordance with an aspect of the present invention, there is provided an apparatus for measuring bio-information of a user, including: an input device for receiving basic bio-information of the user, a first light source arranged on the surface of the skin for radiating a first light having a first wavelength on the surface of the skin, a second light source arranged on the surface of the skin for radiating a second light having a second wavelength on the surface of the skin; a third light source arranged on the surface of the skin in such a manner as to be placed in a more distant position from a photo detector than the first and the second light sources, and radiating a third light having a third wavelength on the surface of the skin, the photo detector detecting detection lights associated with said first through third lights, all of which transmitted through the surface of the skin and converted to electrical signals and a control unit for enabling the first to the third light sources to be driven in a known order and for producing bio-information of the user on the basis of the basic bio-information and intensities of the first to the third detection lights.

In accordance with another aspect of the present invention, there is provided an apparatus for measuring bio-information of a user, including an input device for receiving basic bio-information of the user, a first light source arranged on the surface of the skin radiating a first light having a first wavelength onto the surface of the skin, a second light source arranged on the surface of the skin and radiating a second light having a second wavelength onto the surface of the skin, a first photo detector for sequentially detecting a first detection light and a second detection light, which are transmitted through the surface of the skin and converted to electrical signals, a second photo detector for detecting a third detection light, transmitted through the surface of the skin and converted to an electrical signal and a control unit for enabling the first and the second light sources to be driven in an known order and for producing bio-information of the user on the basis of the basic bio-information and intensities of the first to the third detection lights.

BRIEF DESCRIPTION OF THE DRAWINGS

The above and other exemplary features, aspects, and advantages of the present invention will be more apparent from the following detailed description taken in conjunction with the accompanying drawings, in which.

DETAILED DESCRIPTION OF THE INVENTION

Exemplary embodiments of the present invention are described in detail with reference to the accompanying drawings. The description includes particulars, such as specific configuration elements that are provided to facilitate more comprehensive understanding of the present invention, and it will be obvious to those of ordinary skill in the art that prescribed changes in form and modifications may be made to the particulars in the scope of the present invention. Further, in the following description of the present invention, a detailed description of known functions and configurations incorporated herein are omitted when it may make the subject matter of the present invention rather unclear.

Figure 1:
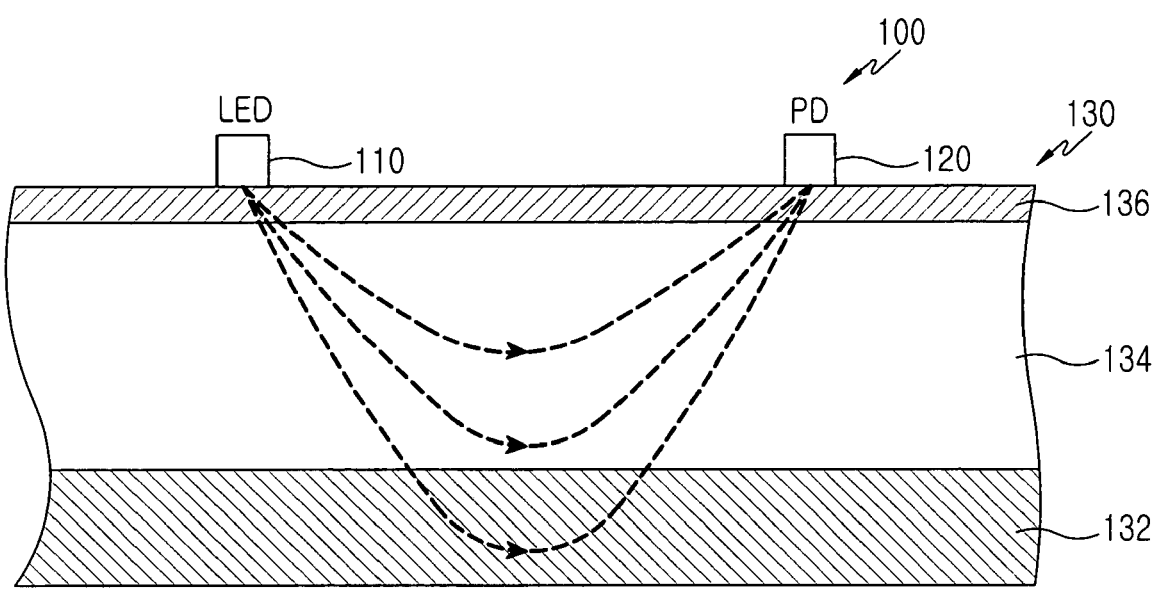
FIG. 1 is a view illustrating an apparatus for measuring the thickness of subcutaneous fat according to the prior art.
Figure 2:
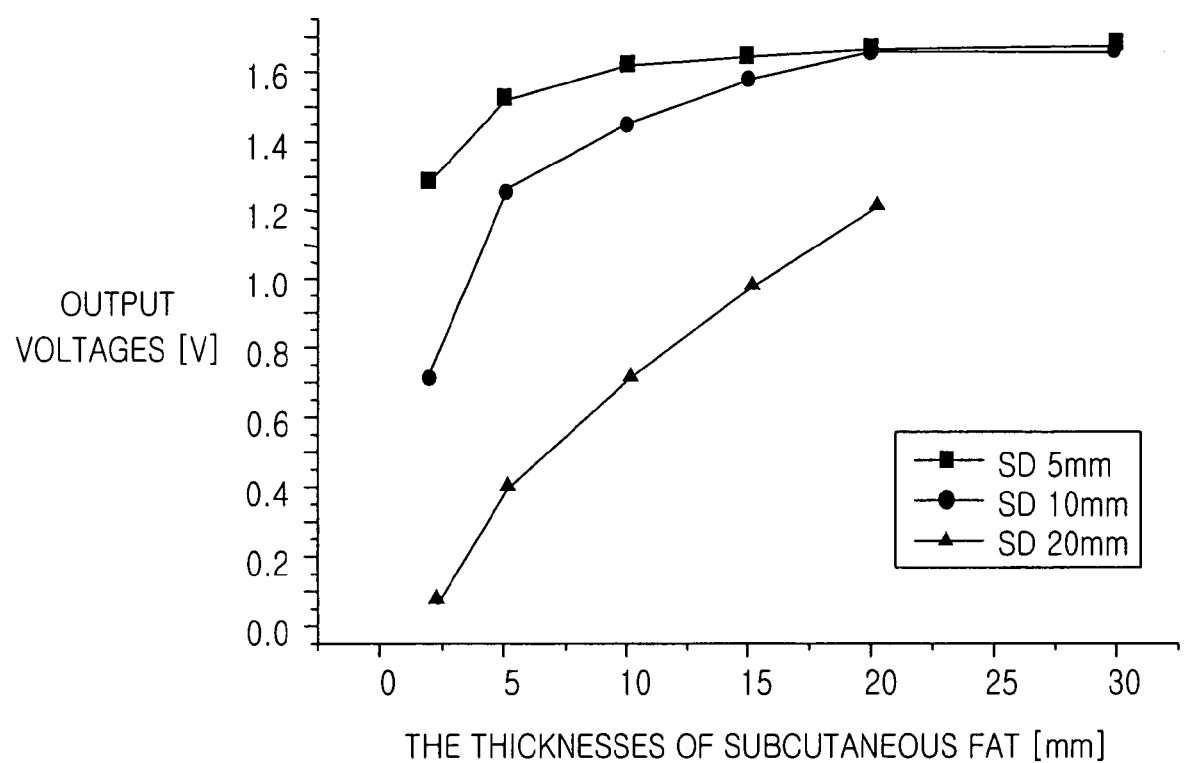
FIG. 2 is a graph illustrating a change in the output of the PD as a function of the thickness of the subcutaneous fat according to separation distances from the LED.
Figure 3:
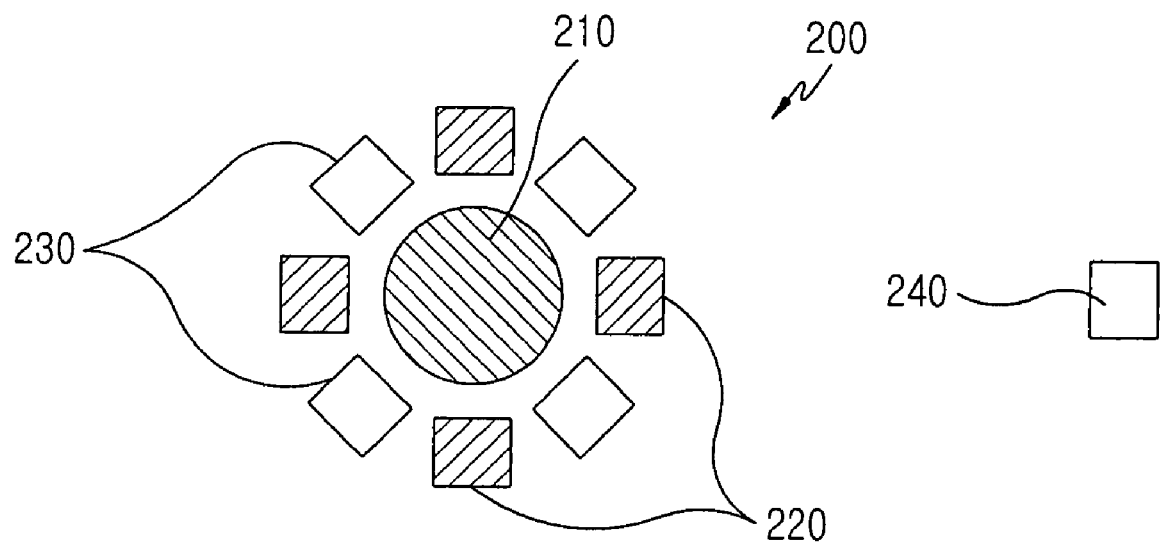
FIG. 3 is a plane view illustrating an apparatus for measuring bio-information according to a first exemplary embodiment of the present invention.
Figure 4:
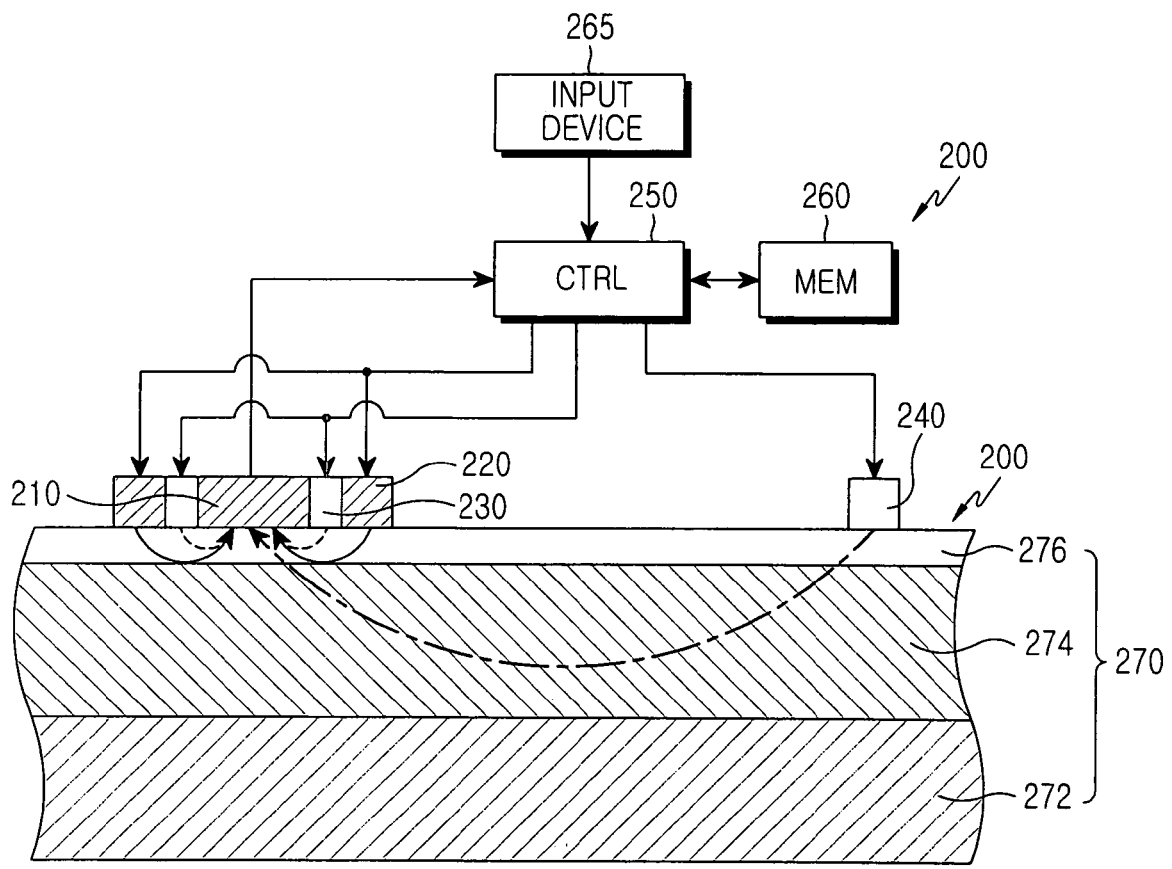
FIG. 4 is a sectional view illustrating the apparatus for measuring bio-information depicted in FIG. 3.

FIG. 3 is a plane view illustrating an apparatus for measuring bio-information according to a first exemplary embodiment of the present invention, and FIG. 4 is a sectional view illustrating the apparatus for measuring bio-information depicted in FIG. 3. Biological tissue 270 has a structure in which respective layers corresponding to muscle 272, subcutaneous fat 274, and skin 276 are laminated in that order. The apparatus 200 for measuring bio-information includes a photo detector 210, multiple first light sources 220, multiple second light sources 230, a third light source 240, a Memory (MEM) 260, an input device 265, and a Controller (CTRL) 250. In FIG. 3, the controller 250, the memory 260, and the input device 265 all of which are depicted in FIG. 4 are not illustrated.

The photo detector 210 is arranged on the surface of the skin 276, and outputs an electrical signal converted by photoelectric conversion from an input light. That is, the photo detector 210 detects input light that is transmitted through the surface of the skin 276 and converts the detected light to an electrical signal. The photo detector 210 is equipped with a light receiving surface at the lower end thereof, and the light receiving surface of the photo detector 210 can tightly contact with the surface of the skin 276, or can be separate from the skin. A conventional photo diode can be used as photo detector 210.

Around the photo detector 210, one or more (four '4' as an exemplary embodiment) first light sources 220 and one or more (four '4' as an exemplary embodiment) second light sources 230 are arranged alternately, where the first light sources 220 and the second light sources 230 are separate from the photo detector 210 by the same distance, and are arranged at the same intervals in a circumferential direction. That is, in a direction perpendicular to the direction of a diameter thereof with the photo detector 210 as the center.

Each of the first light sources 220 is arranged on the surface of the skin 276 so as to be separate from the photo detector 210, and radiates a first light (denoted in a solid line) having a first wavelength (e.g., 660 nm) in a band (desirably, 600 to 750 nm) of visible light on the surface of the skin 276. The first light source 220 is equipped with a light emitting surface at the lower end thereof, and the light emitting surface of the first light source 220 can tightly contact with the surface of the skin 276, or can be separate from the surface of the skin. As the first light source 220, a conventional LED or Laser Diode (LD) can be used.

Each of the second light sources 230 is arranged on the surface of the skin 276 so as to be separate from the photo detector 210, and radiates a second light (denoted in a dotted line) having a second wavelength (e.g., 880 nm) in a band (desirably, 750 to 1,000 nm) of near infrared rays on the surface of the skin 276. The second light source 230 is equipped with a light emitting surface at the lower end thereof, and the light emitting surface of the second light source 230 can tightly contact with the surface of the skin 276, or can be separate from the surface of the skin. As the second light source 230, a conventional LED or LD can be used.

The third light source 240 is arranged on the surface of the skin 276 in such a manner as to be placed in a more distant position from photo detector 210 than the first and the second light sources 220 and 230, and radiates a third light (denoted as an alternated long and short dash line) having a third wavelength in the band of near infrared rays on the surface of the skin 276. The third light source 240 is equipped with a light emitting surface at the lower end thereof, and the light emitting surface of the third light source 240 can tightly contact with the surface of the skin 276, or can be separate from the surface of the skin. As the third light source 240, a conventional LED or LD can be used. In the present embodiment, the third wavelength is set so as to be the same as the second wavelength.

Each of the photo detector 210, the first light sources 220 and the second light sources 230, and the third light source 240 can be separate from the skin, but in this case, optical coupling efficiency and the accuracy of measurement caused by an alignment error can be reduced.

In the present embodiment, a typical distance between the photo detector 210 and the first and second light sources 220 and 230 equals 2 millimeters (mm), and a distance between the photo detector 210 and the third light source 240 equals 10 mm. Desirably, a distance between the photo detector 210 and the first and second light sources 220 and 230 is equal to or shorter than 5 mm, and a distance between the photo detector 210 and the third light source 240 is equal to or longer than 10 mm. Since the first and the second light sources 220 and 230 are used to measure information about the skin 276, in order to reduce the influence of the thickness of the subcutaneous fat 274, it is desirable that the distance between the photo detector 210 and the first and second light sources 220 and 230 is set so as to be equal to or shorter than 5mm. Also, since the third light source 240 is used to measure information about the subcutaneous fat layer 274, so that measuring a wide range of the thickness of the subcutaneous fat can be accomplished, it is desirable that the distance between the photo detector 210 and the third light source 240 is set so as to be equal to or longer than 10 mm.

Collagen fiber included in the skin 276 has an unsymmetrical optical characteristic. In the present embodiment, while multiple first light sources 220 are arranged evenly around the photo detector 210 in order to offset a directional characteristic of the skin 276, a single first light source 220 can be used. For the same reasons as above, a single second light source 230 can be used.

A light received by the photo detector 210 among the first lights is specifically referred to as a "first detection light", a light received by the photo detector 210 among the second lights is specifically referred to as a "second detection light", and a light received by the photo detector 210 among the third light is specifically referred to as a "third detection light."

Skin color is largely influenced by a Melanin Index (MI) and an erythema index. The MI is used to classify a human race, and the erythema index is determined by a distribution of capillary vessels and a distribution of blood existing in the skin. The erythema index is easily affected by pressure applied to the skin, and has such a tendency that variations classified by individuals are largely reduced due to blocking blood if the pressure is strong. Under these conditions, skin color can be represented by using only the MI.

The MI can be defined by the following equation (1):

$$MI = A + B \ln(I_1/I_2) \quad (1)$$

where A and B represent first coefficients,
$I_1$ represents the intensity of the first detection light,
$I_2$ represents the intensity of the second detection light; and
ln represents a natural logarithmic function.

The first coefficients A and B are found through numerical analysis such as a least square method, and at this time, an MI (hereinafter, an MI obtained by a commercial apparatus is referred to as a "standard MI") obtained by a commercial apparatus for diagnosing skin color (e.g., a Mexameter MX18 manufactured by CK Electric company).

In providing numerical examples accompanied by various algorithms proposed in the present invention, experimental conditions are adopted as a premise.

As the first light sources 220, an OPA6611 LED chip that the Knowledge-on company in Korea (See Web Site: http://www.knowledge-on.com) has released is used, having a maximum current value equal to 145 milli-amperes (mA) while being driven with a pulse whose duty cycle is 8%. As the second light sources 230, an OPA8732HP(F) LED chip that the Knowledge-on company has released is used, having a maximum current value equal to 28 mA while being driven with a pulse whose duty cycle is 8%. As the third light source 240, an OPA8750T LED chip that the Knowledge-on company has released is used, having a maximum current value equal to 290 mA while being driven with a pulse whose duty cycle is 8%. As the photo detector 210, an HPI-12N silicon photo diode that the Kodenshi Korea company has released is used, which has a chip size of 1.2 mm×1.2 mm. A separation distance between the photo detector 210 and the first and second light sources 220 and 230, in one aspect of the invention, equals 2 mm, and a separation distance between the photo detector 210 and the third light source 240 equals 25 mm. The intensity (i.e., optical power) of each detection light corresponds to the value computed by subtracting an intensity (the intensity of an ambient light, such as natural light, lighting, etc.) measured by the photo detector 210, in a state where relevant light sources stop operating, from an intensity detected by the photo detector 210 in a state where relevant light sources operate. A clinical trial has been conducted with adult males in the age range of twenty to fifty and adult females in the age range of twenty to thirty as a target.

NUMERICAL EXAMPLE 1

Figure 5:
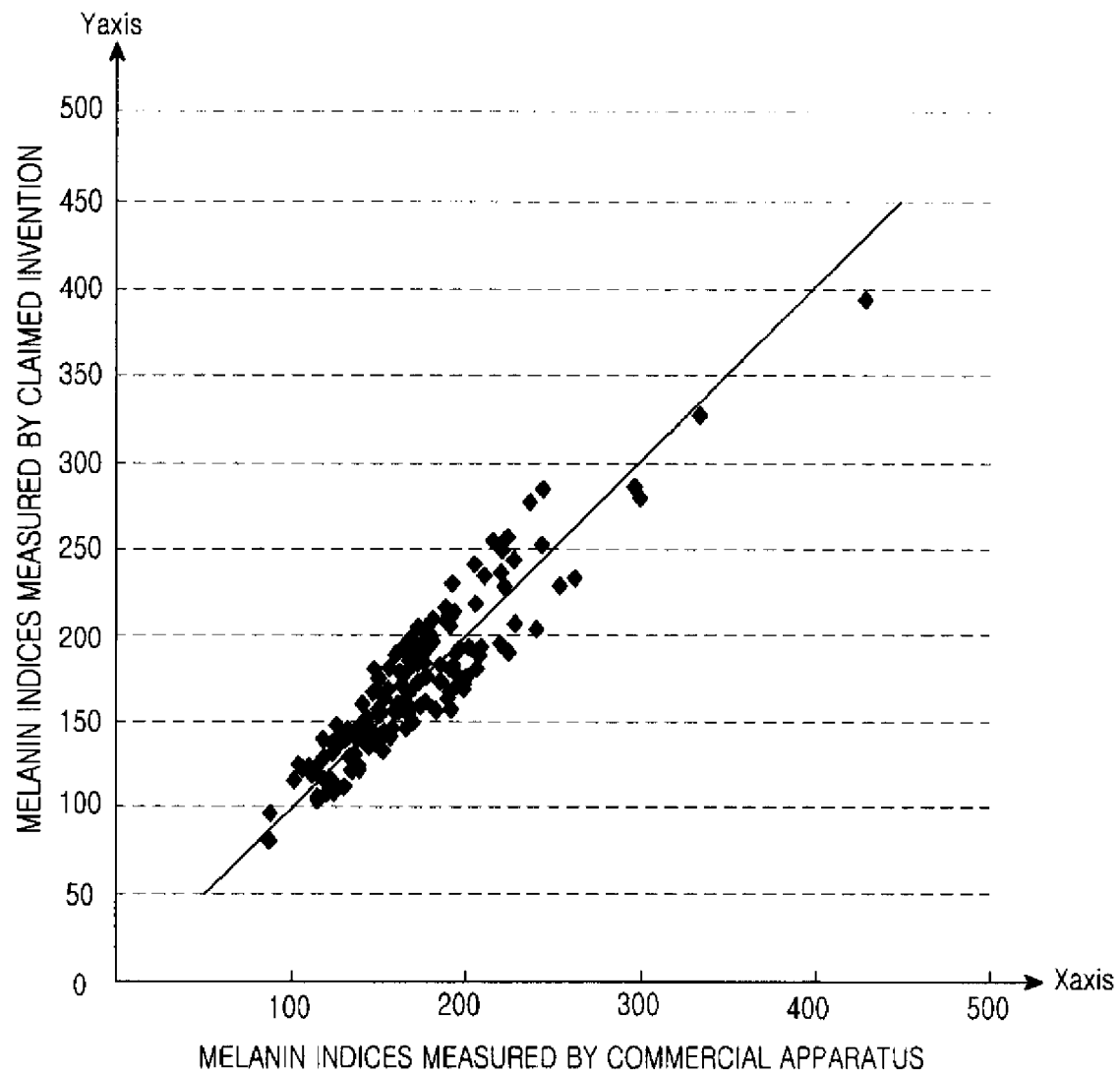
FIG. 5 is a graph illustrating a correlation between a standard Melanin Index (MI) measured by a commercial apparatus and an MI measured by the apparatus for measuring bio-information depicted in FIG. 4.

FIG. 5 is a graph illustrating a correlation between a standard Melanin Index (MI) measured by a commercial apparatus and an MI measured by the apparatus, in accordance with the principles of the invention, for measuring bio-information.

In FIG. 5, the X axis represents a standard Melanin Index (MI) measured by the commercial apparatus, and the Y axis represents an MI measured by the apparatus 200 for measuring bio-information. Each MI measured by the apparatus 200 is represented as a small square. In the present numerical example 1, a measured MI is computed by using equation (1), and the respective first coefficients A and B are set to '280.14' and '−575.01.' The two melanin indices A and B show a correlation coefficient of about '0.921.'

The intensity of a detection light detected by the photo detector 210 varies depending on the color and the thickness of the skin 276, and in addition to this, optical characteristics, such as sex, age, height, weight, and the like, that affect the intensity of a detection light.

The Subcutaneous Adipose Tissue (SAT) of the subcutaneous fat 274 is given as a function of optical characteristics that an intensity $I_3$ of the third detection light having a wavelength of 880 nm, the skin 276, the subcutaneous fat 274, and the muscle 272 have, and is defined by the following equation (2):

$$SAT = f(I_3, GEN, AGE, HT, WT, SC, ST) \quad (2),$$

where GEN represents sex distinction, AGE represents age, HT represents height, WT represents weight, SC represents skin color, and ST represents the thickness of the skin.

Figure 6:
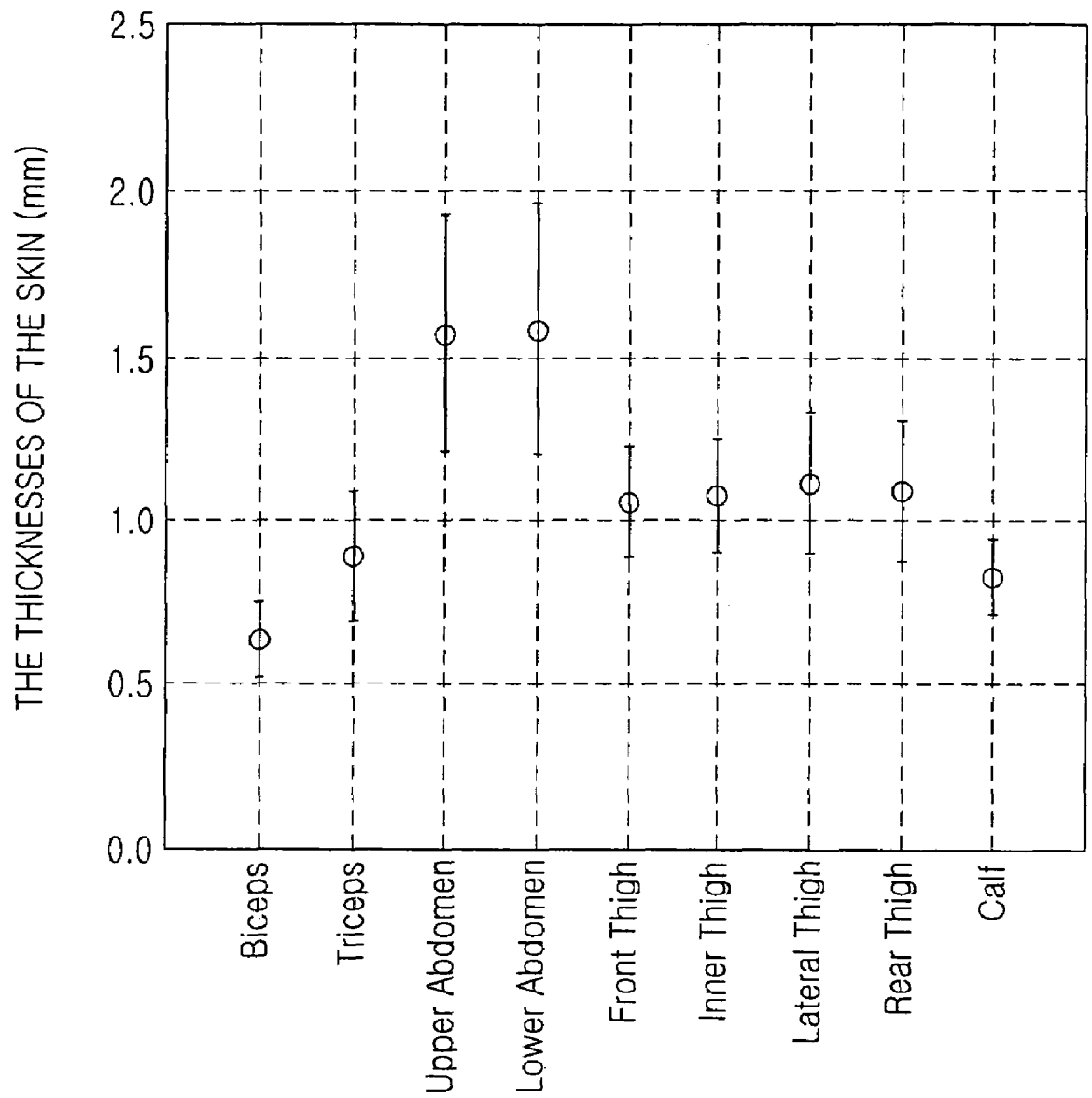
FIG. 6 is a graph illustrating changes of the thickness of the skin corresponding to measurement positions.

FIG. 6 is a graph illustrating changes of the thickness of the skin corresponding to measurement positions. The thickness of the skin has been measured by using Computerized Tomography (CT), and with 34 Korean females in their twenties as a target, biceps, triceps, upper abdomen, lower abdomen, front thigh, inner thigh, lateral thigh, rear thigh, and calf have been measured. As illustrated, since a variation of the thickness of the skin in each measurement position is not large, in equation (2), it is possible to substitute the thickness of the skin with a measurement position.

$$SAT = f(I_3, GEN, AGE, HT, WT, SC, POS) \quad (3),$$

where POS denotes a measurement position.

As expressed in equation (4), skin color can be substituted by an MI, and height (HT) and weight (WT) can be represented by using a Body Mass Index (BMI).

$$SAT = f(I_3, GEN, AGE, BMI, MI, POS), \text{ and} \quad (4)$$

$$BMI = WT[Kg]/HT^{2[m]}$$

In equation (4), if the intensity of the third detection light, the BMI, and the MI are specified as variables and the remaining factors are specified as coefficients, equation (4) can be represented as:

$$SAT_P = f_P(I_3, BMI, MI) \quad (5)$$

where $SAT_P$ represents the thickness of subcutaneous fat classified by measurement positions.

Also, equation (5) can be expressed as $$SAT_P = f_P(I_{MI}, BMI) \text{ and}$$

$$I_{MI} = I_3/(I_1/I_2) \quad (6)$$

In equation (6), a function $f_P$ is specifically expressed as the following equation (7).

$$SAT_P = f_P(I_{MI}, BMI) = C_P + D_P BMI + E_P I_{MI} \quad (7)$$

In equation (7), second coefficients $C_P$, $D_P$, and $E_P$ can be found through multiple regression analysis in which, with sex distinction, age, and measurement positions specified as constants, a process for substituting $SAT_P$ measured by CT, $I_{MI}$ measured by the apparatus 200 and BMI obtained by a user's input into equation (7) is repeated. The multiple regression analysis can also be applied to equation (5).

Figure 7:
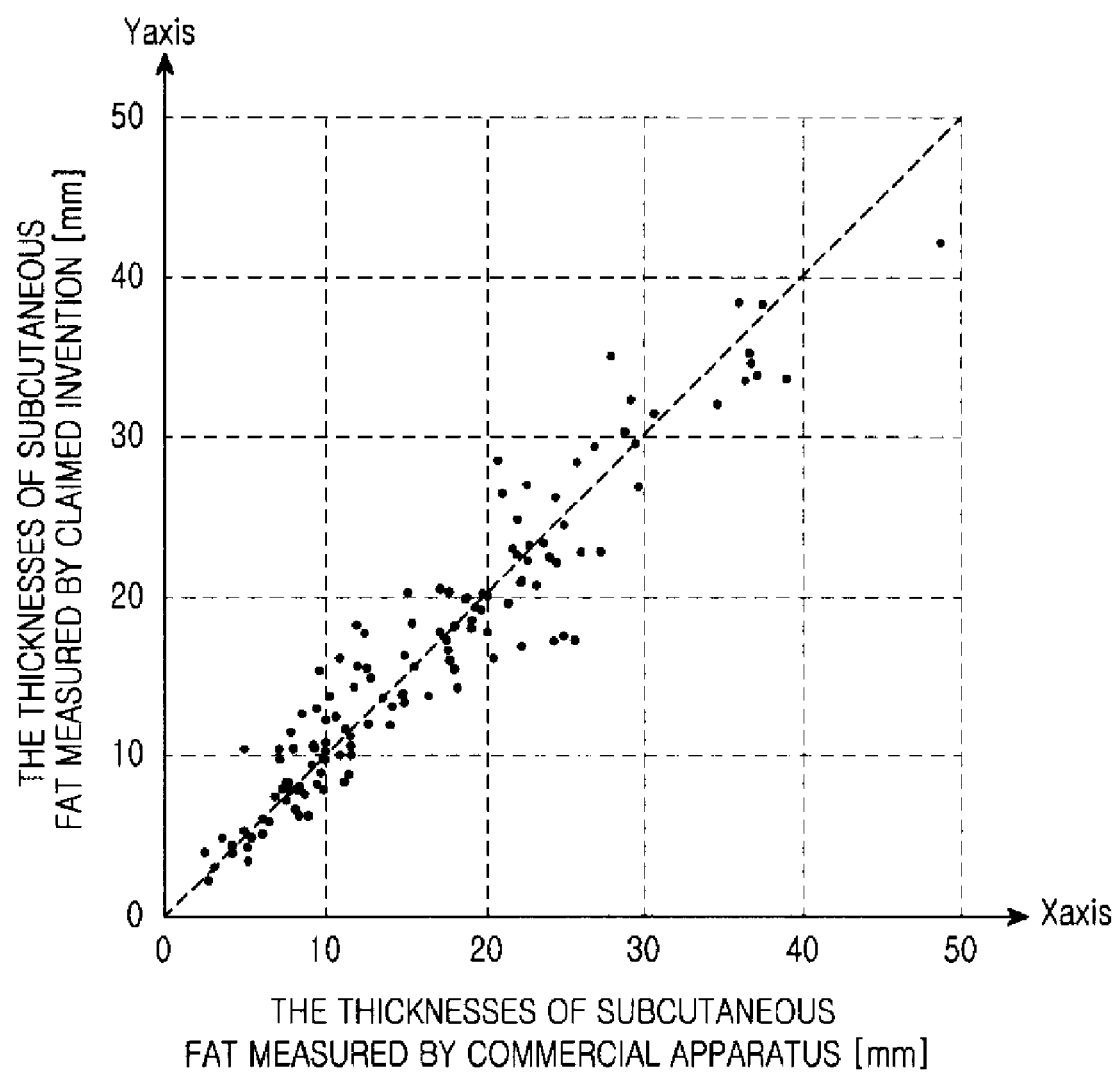
FIGS. 7 to 9 are graphs illustrating correlations between standard thicknesses of subcutaneous fat measured by a commercial apparatus and thicknesses of subcutaneous fat measured by the apparatus for measuring bio-information depicted in FIG. 4.

FIG. 7 is a graph illustrating a correlation between the standard thickness of subcutaneous fat measured by a commercial apparatus and the thickness of subcutaneous fat measured by the apparatus 200.

In FIG. 7, the X axis represents the standard thickness of subcutaneous fat measured by a commercial apparatus (e.g., an ultrasonic apparatus), and the Y axis represents the thickness of subcutaneous fat measured by the apparatus 200. The standard thickness and the thickness of subcutaneous fat have a correlation coefficient of about '0.95'therebetween. The thickness of subcutaneous fat has been measured by using CT, and with 13 Korean females in their twenties as a target, biceps, triceps, upper abdomen, lower abdomen, front thigh, inner thigh, lateral thigh, rear thigh, and calf have been measured.

NUMERICAL EXAMPLE 2

Figure 8:
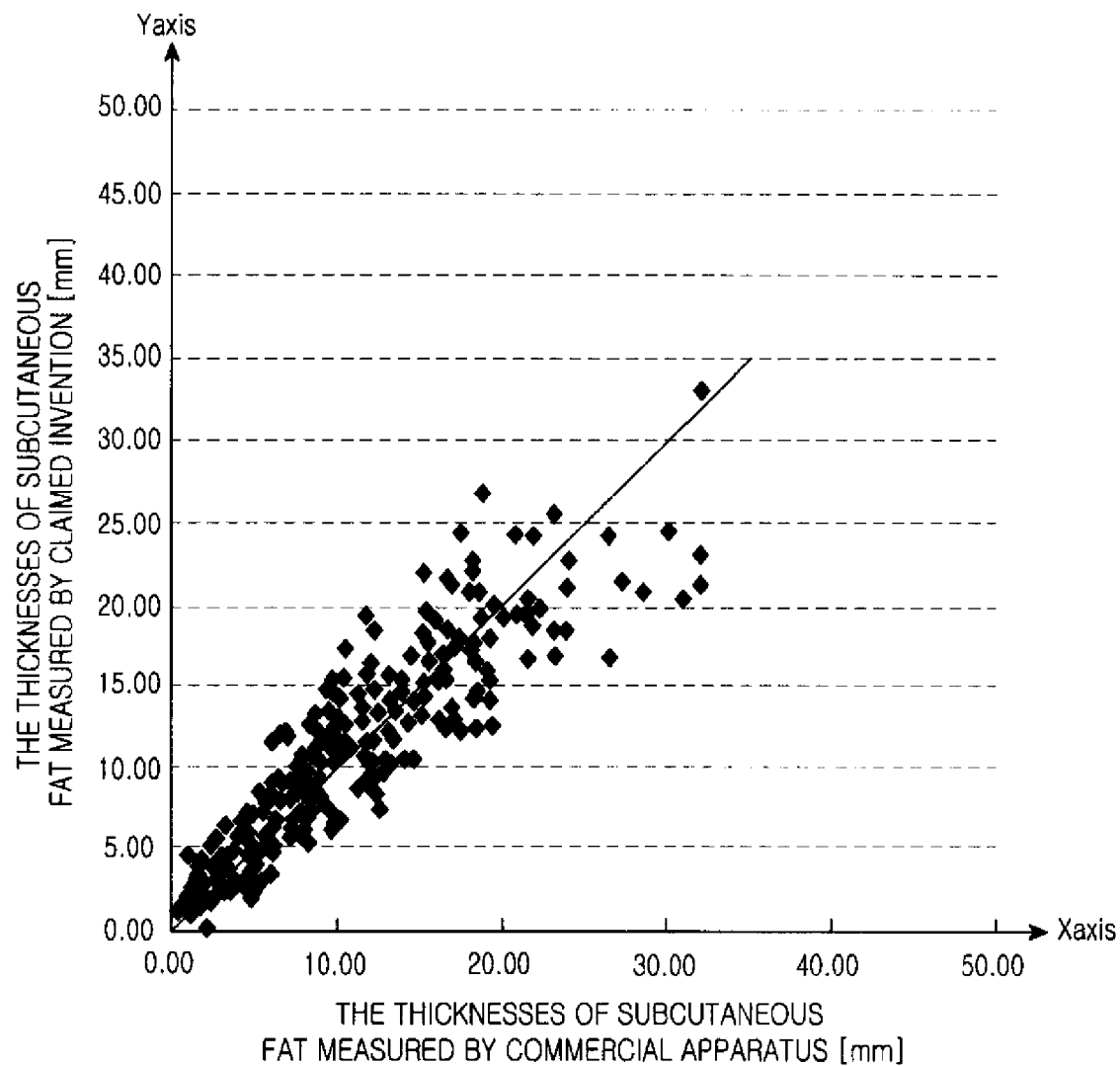

FIG. 8 is a graph illustrating a correlation between the standard thickness of subcutaneous fat measured by a commercial apparatus and the thickness of subcutaneous fat measured by the apparatus 200.

In FIG. 8, the X axis represents the standard thickness of subcutaneous fat measured by a commercial apparatus, and the Y axis represents the thickness of subcutaneous fat measured by the apparatus 200 in accordance with the principles of the invention. Each thickness of subcutaneous fat measured by the apparatus 200 is represented as a small square, and a clinical trial has been conducted with males as a target. In the present numerical example 2, each measured thickness of subcutaneous fat has been computed by using equation (7), and the second coefficients $C_P$, $D_P$, and $E_P$ are given as in TABLE 1, depending on measurement positions. The standard thickness and the thickness of subcutaneous fat have a correlation coefficient of about '0.932' therebetween.

TABLE 1

|  | $C_P$ | $D_P$ | $E_P$ |
|---|---|---|---|
| biceps | −3.016 | 0.159 | 25.705 |
| calf | 0.693 | 0.062 | 23.506 |
| front thigh | −4.756 | 0.325 | 22.841 |
| lower abdomen | −27.105 | 1.592 | 24.771 |
| flank | −3.075 | 0.404 | 16.865 |
| triceps | −2.327 | 0.180 | 15.673 |

NUMERICAL EXAMPLE 3

Figure 9:
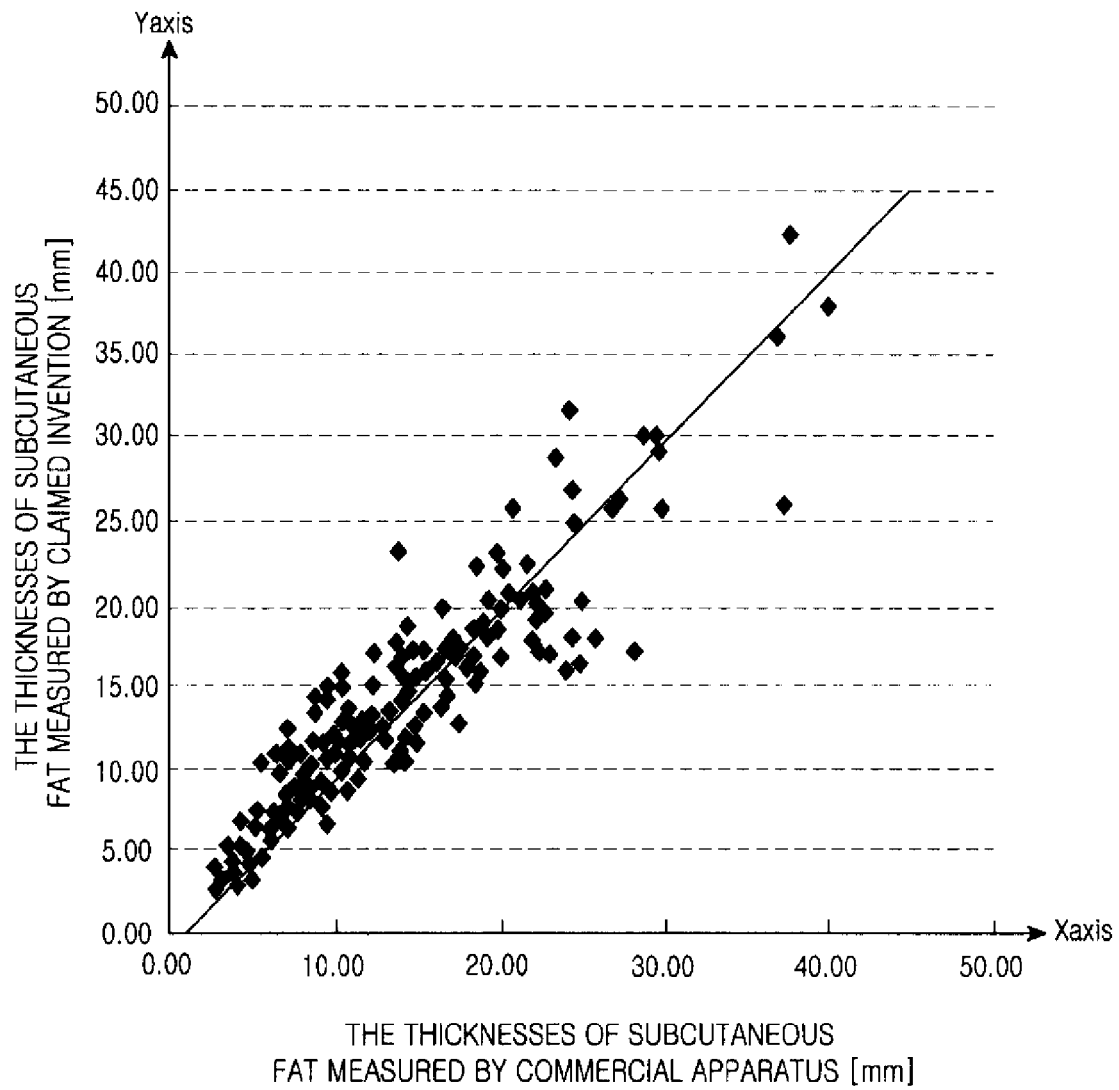

FIG. 9 is a graph illustrating a correlation between the standard thickness of subcutaneous fat measured by a commercial apparatus and the thickness of subcutaneous fat measured by the apparatus 200.

In FIG. 9, the X axis represents the standard thickness of subcutaneous fat measured by a commercial apparatus, and the Y axis represents the thickness of subcutaneous fat measured by the apparatus 200 for measuring bio-information. Each thickness of subcutaneous fat measured by the apparatus 200 for measuring bio-information is represented as a small square, and a clinical trial has been conducted with females as a target. In the present numerical example 3, each measured thickness of subcutaneous fat has been computed by using equation (7), and the second coefficients $C_P$, $D_P$, and $E_P$, depending on measurement positions, are given as in TABLE 2. The standard thickness and the thickness of subcutaneous fat have a correlation coefficient of about '0.926'therebetween.

TABLE 2

|  | $C_P$ | $D_P$ | $E_P$ |
|---|---|---|---|
| biceps | −5.680 | 0.490 | 6.989 |
| calf | 2.507 | 0.155 | 18.304 |
| front thigh | −5.244 | 0.446 | 15.410 |
| inner thigh | −7.443 | 0.959 | 14.074 |
| lower abdomen | −20.776 | 1.709 | 25.000 |
| flank | −13.463 | 1.213 | 6.909 |
| triceps | −7.170 | 0.772 | 8.265 |

A percent body fat can be defined by the following equation (8).

$$PBF_P = F_P + G_P BMI + H_P AGE + I_P I_{MI} \quad (8)$$

In equation (8), third coefficients $F_P$, $G_P$, $H_P$, and $I_P$ can be found through multiple regression analysis in which, with sex distinction and measurement positions specified as constants, a process for substituting $PBF_P$ measured by CT, $I_{MI}$ measured by the apparatus 200 for measuring bio-information, and both AGE and BMI obtained by a user's input into equation (8) is repeated.

NUMERICAL EXAMPLE 4

Figure 10:
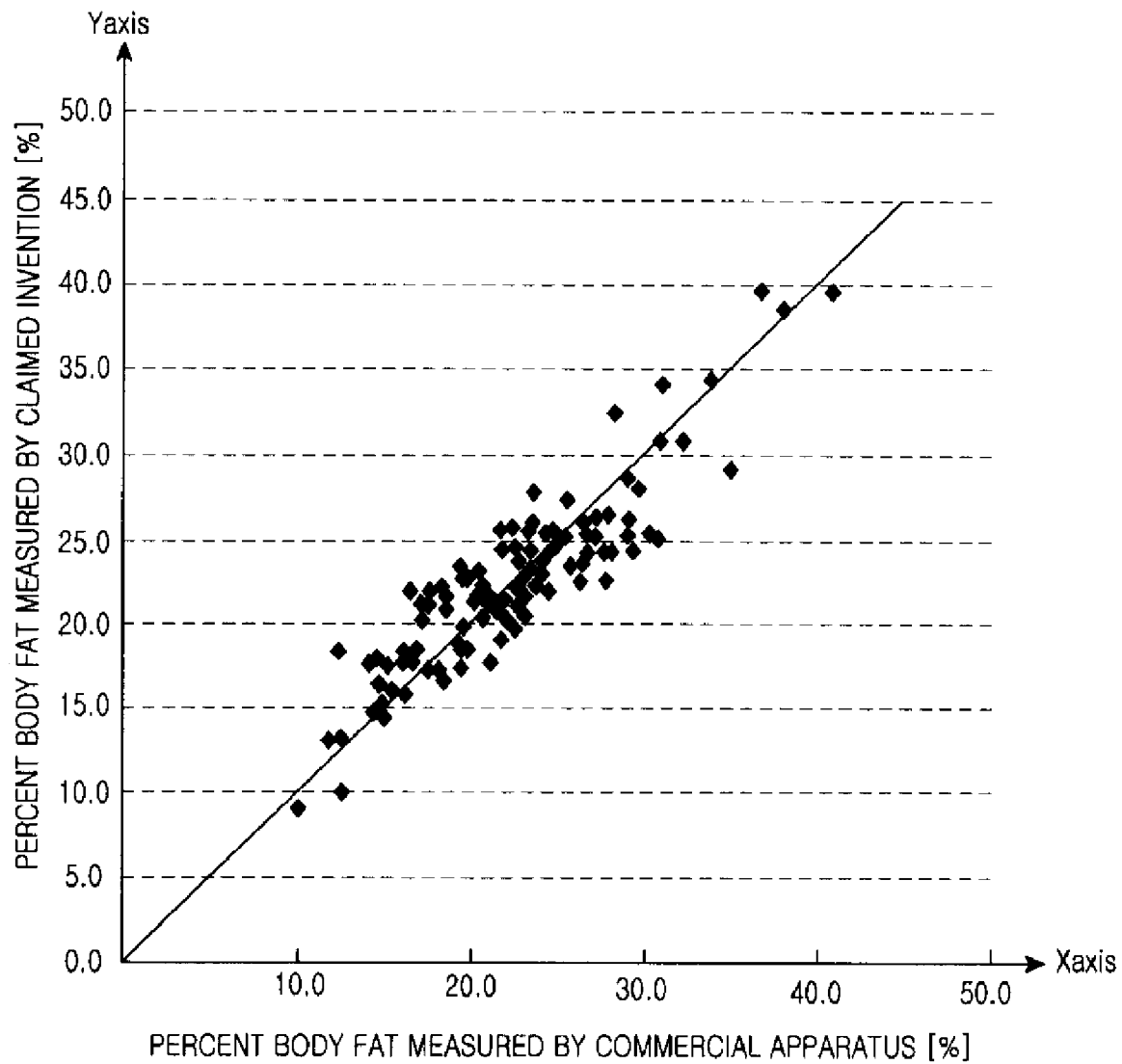
FIG. 10 is a graph illustrating a correlation between a percent body fat measured by a commercial apparatus and a percent body fat measured by the apparatus for measuring bio-information.

FIG. 10 is a graph illustrating a correlation between a percent body fat measured by a commercial apparatus and a percent body fat measured by the apparatus 200 for measuring bio-information.

In FIG. 10, the X axis represents a standard percent body fat measured by a commercial apparatus (e.g., a Bioelectric Impedance Analysis (BIA) apparatus), and the Y axis represents the percent body fat measured by the apparatus 200 for measuring bio-information. Each percent body fat measured by the apparatus 200 is represented as a small square, and a clinical trial has been conducted with both males and females as targets. In the present numerical example 3, each measured percent body fat has been computed by using equation (8), the lower abdomen has been measured in the case of every male, and the fleshy inside of the thigh has been measured in the case of every female. In the case of males, the third coefficients $F_P$, $G_P$, $H_P$, and $I_P$ are given respectively as −14.693, 1.303, 0.067 and 10.833, and in the case of females, the third coefficients $F_P$, $G_P$, $H_P$, and $I_P$ are respectively given as −3.009, 1.142, 0.088 and 13.339. The standard percent body fat and the percent body fat have a correlation coefficient of about 0.905 therebetween.

Referring to FIG. 3 again, the input device 265 functions as an interface for receiving basic bio-information, including sex distinction, age, height, weight, etc., from a user. For instance, the input device 256 can be embodied with a keypad conventionally provided to a handheld device, including a wireless mobile terminal and the like.

The memory 260 stores a table required to express relations between the basic bio-information and the second coefficients necessary to compute the basic bio-information and the thickness of subcutaneous fat. Namely, in the table, the basic bio-information (e.g., data sets expressed as {sex distinction, age, and measurement positions}) and coefficient sets (e.g., data sets represented as $\{C_P, D_P, \text{and } E_P\}$) corresponding to the basic bio-information are recorded.

The controller 250 enables the memory 260 to store the basic bio-information provided from the input device 265, enables the first light sources 220, the second light sources 230 and the third light source 240 to be driven one by one, and computes skin color (i.e., an MI) and the thickness of subcutaneous fat on the basis of the intensities of the first to third detection lights sequentially detected by the photo detector 210 and the table. The controller 250 can then compute the percent body fat. To this end, the controller 250 is electrically connected with the photo detector 210, the first light sources 220, the second light sources 230 and the third light source 240, receives an output signal from the photo detector 210, and outputs a driving signal to each of the first light sources 220, the second light sources 230 and the third light source 240. The controller 250 substitutes a BMI computed by equation (4) for height and weight among the basic bio-information provided from the input device 265, and enables the substituted BMI to be stored.

In the present embodiment, while it is exemplified that the first light sources 220, the second light sources 230 and the third light source 240 are driven in turn, drive order can be optionally determined.

Figure 11:
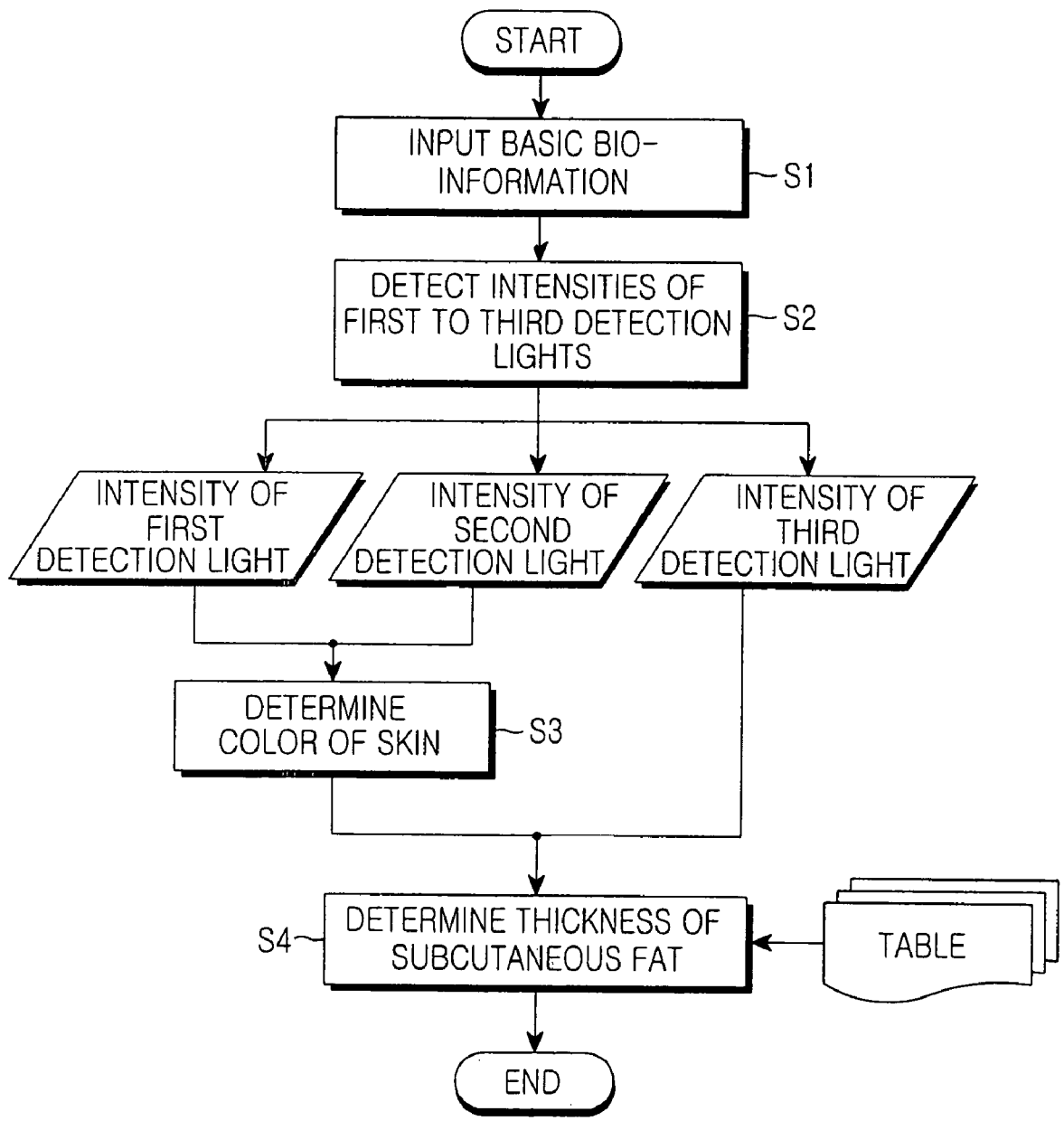
FIG. 11 is a flowchart illustrating a control process of a controller depicted in FIG. 4.

FIG. 11 is a flowchart illustrating a control process of the controller 250. The controller 250 performs the following steps S1 to S4.

In step S1, the basic bio-information, including sex distinction, age, height, weight, measurement positions, etc., is input from a user by using the input device 265.

In step S2, intensities of the first to the third detection lights are detected. The controller 250 enables the first light sources 220, the second light sources 230 and the third light source 240 to be driven in turn, and senses intensities of the first to the third detection lights sequentially detected by the photo detector 210. An electrical signal provided from the photo detector 210 has a voltage level depending on the intensity of light input into the photo detector 210. The controller 250 can correspond to a digital device which is not equipped with an analog/digital interface, or the photo detector 210, the first light sources 220, the second light sources 220, and the third light source 240 can correspond to analog devices which are not equipped with an analog/digital interface. In this case, an analog-to-digital converter can be connected between the controller 250 and the photo detector 210, and a digital-to-analog converter can be connected between the controller 250 and each of the first to the third light sources 220, 230, and 240.

In step S3, skin colors equivalent to the intensities of the first and the second detection lights are determined. Skin color (i.e., an MI) can be computed by substituting the intensities of the first and the second detection lights into equation (1).

In step S4, the thickness of subcutaneous fat is determined on the basis of the basic bio-information, the intensities of the first to the third detection lights, and the values stored in a table as described above.

First, the controller 250 determines three coefficients corresponding to the basic bio-information. This step can be regarded as a process for mapping the basic bio-information to the three coefficients. Since the table has discrete data sets (i.e., {sex distinction, age, and measurement positions} and $\{C_P, D_P, \text{and } E_P\}$), if the basic bio-information is given, the three coefficients corresponding to the basic bio-information can be determined through an approximation algorithm. For example, basic bio-information which is the most approximate to basic bio-information given in the table is found, or three coefficients which are approximate through interpolation can be computed.

Second, the controller 250 substitutes the three determined coefficients, the intensities of the first to the third detection lights, and the BMI (or height and weight) into equation (7), and then computes the thickness of subcutaneous fat.

Subsequently, the controller 250 can display skin color and the thickness of subcutaneous fat. To this end, the apparatus 200 for measuring bio-information can further include a display device, such as a Liquid Crystal Display (LCD), which is electrically connected with the controller 250.

The apparatus 200 for measuring bio-information according to the present invention can be applied to a mobile terminal or a wearable device, such as a mobile phone, a Personal Digital Assistant (PDA), etc., and can be modularized so as to form a single body with the mobile terminal or so as to be installable into the mobile terminal. The apparatus 200 may include at least one photo detector 210, at least one first light source 220, at least one second light source 230, at least one third light source 240 and a controller 250, and the output of the photo detector 210 is output to a mobile phone by wire, or the output of the photo detector 210 can be output to a mobile terminal\wirelessly using an antenna. In such cases, the controller 250 performs only the function for enabling the first light sources 220, the second light sources 230 and the third light source 240, and since a mobile terminal is conventionally equipped with a control unit and a memory, the control unit of the mobile terminal can perform steps for computing the above-described skin color and the thickness of subcutaneous fat.

When considering a directional characteristic of biological tissue, it is necessary that not only the number of the first and the second light sources 220 and 230, but also the number of the third light sources 240 increase in order to surround the photo detector 210.

However, since a manufacturing cost of the apparatus 200 for measuring bio-information increases in the above case, in the following embodiments, structures will be proposed in which the number of light sources is minimized by using a waveguide, and simultaneously, errors caused by a directional characteristic of biological tissue can be corrected.

Figure 12:
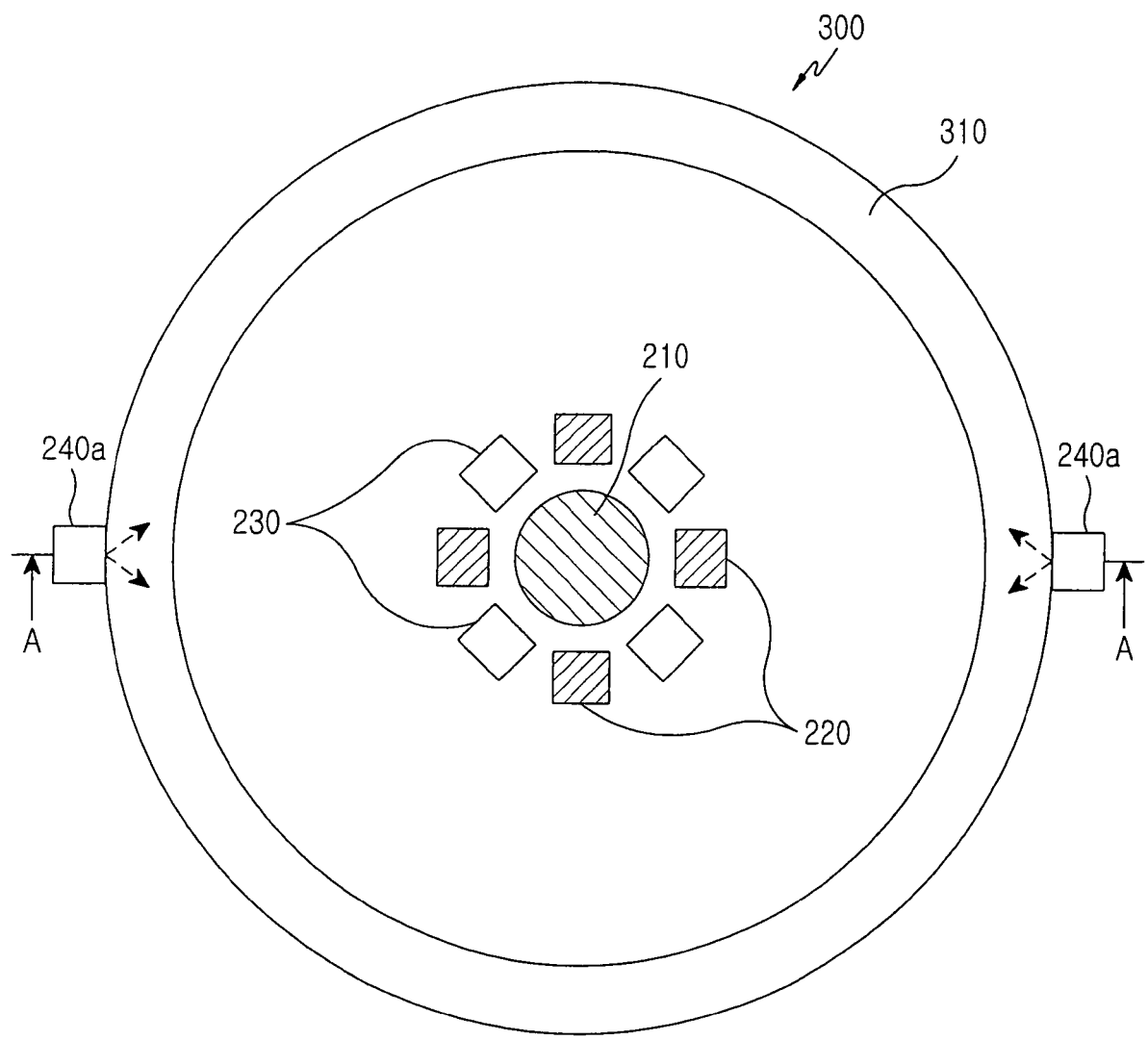
FIG. 12 is a plane view illustrating an apparatus for measuring bio-information according to a second exemplary embodiment of the present invention.
Figure 13:
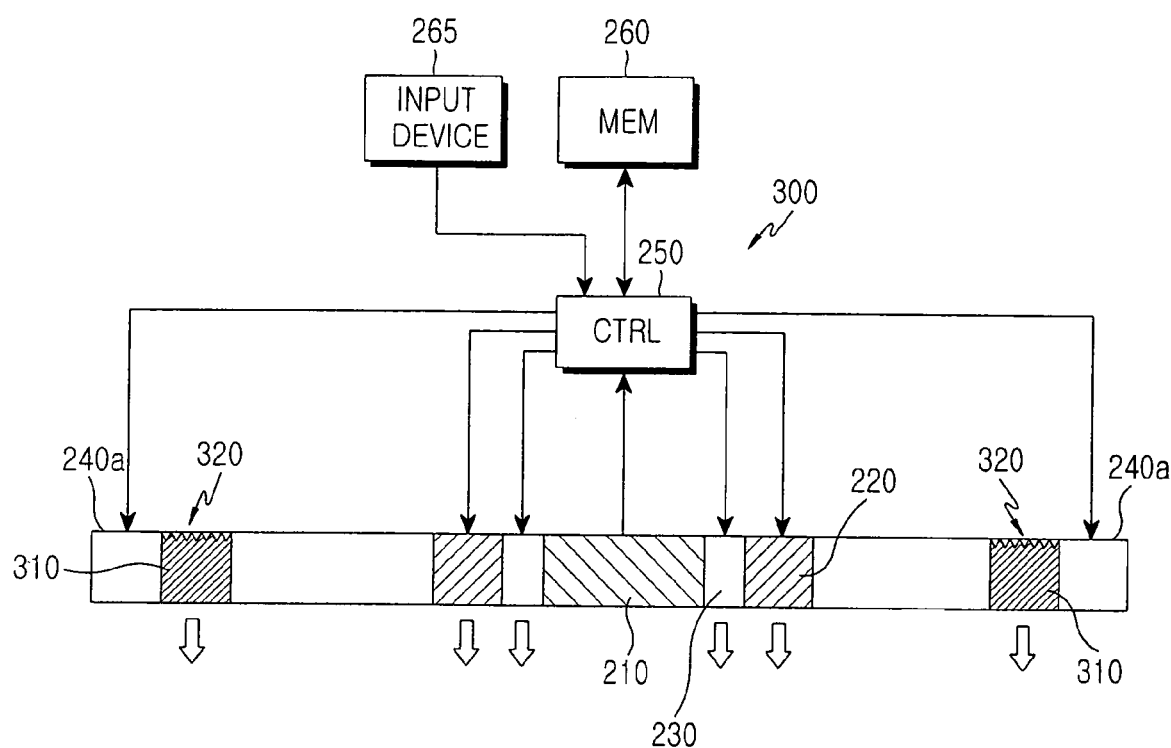
FIG. 13 is a sectional view of the apparatus for measuring bio-information taken along a line A-A in FIG. 12.

FIG. 12 is a plane view illustrating an apparatus for measuring bio-information according to a second exemplary embodiment of the present invention, and FIG. 13 is a sectional view taken along line A-A in the apparatus for measuring bio-information. Since the apparatus 300 for measuring bio-information has a configuration and the functions similar to those of the apparatus 200 depicted in FIG. 3 the difference between the apparatus 200 and the apparatus 300 is a larger number of third light sources 240A and a larger number of waveguides. Similar elements will be designated by the same reference numerals, and an overlapping description will be omitted. The apparatus 300 for measuring bio-information includes a photo detector 210, multiple first light sources 220, multiple second light sources 230, multiple third light sources 240A, a waveguide 310, a memory 260, an input device 265, and a controller 250. In FIG. 12, the controller 250, the memory 260, and the input device 265 which are depicted in FIG. 13 are not illustrated.

The photo detector 210 is arranged on the surface of the skin (not shown), and outputs an electrical signal that is converted by photoelectric conversion from an input light. The photo detector 210 detects light radiating from the surface of the skin and outputs an electrical signal.

Positioned around the photo detector 210, the first four light sources 220 and the second four light sources 230 are arranged alternately, where the first four light sources 220 and the second four light sources 230 are separate from the photo detector 210 at the same distance, and are arranged at the same intervals in a circumferential direction.

Each of the four first light sources 220 is arranged on the surface of the skin so as to be separate from the photo detector 210, and radiates a first light having a first wavelength (e.g., 660 nm) in the band of visible light on the surface of the skin.

Each of the four second light sources 230 is arranged on the surface of the skin so as to be separate from the photo detector 210, and radiates a second light having a second wavelength (e.g., 940 nm) in the band of near infrared rays on the surface of the skin.

The waveguide 310 has a shape of a circular ring, is arranged on the surface of the skin so as to surround the photo detector 210 and the first and second light sources 220 and 230, has an inner circumferential surface and an outer circumferential surface opposite each other, and has an upper surface and a lower surface opposite each other. At this time, the lower surface of the waveguide 310 functions as an output end, and can be in tight contact with the surface of the skin or can separate from it. A sectional surface perpendicular to a circumferential direction (i.e., a direction perpendicular to the direction of a diameter of the waveguide 310) thereof has a square shape. The waveguide 310 has a larger refractive index than air or the skin, and light travels in the manner of total reflection in a circumferential direction inside the waveguide 310. The waveguide 310 can be implemented by using material, such as polycarbonate, acryl-based resin, etc. that has a transparent characteristics with respect to a wavelength of a third light, and can be manufactured by injection molding or other similar methods. Otherwise, the waveguide 310 can be embodied with rubber material that has a transparent characteristic with respect to the wavelength of the third light, and preferably, can be realized with material such as polyurethane, silicon, and the like.

The upper surface of the waveguide 310 is equipped with multiple light extracting patterns 320 formed to output light traveling to the inside of the waveguide 310 to the outside of the waveguide 310 through the lower surface thereof. Each of the light extracting patterns 320 scatters an incident light. The light extracting patterns 320 are formed symmetrically with the center of curvature of the waveguide 310 as the reference. By destroying a total internal reflection condition at a boundary between the waveguide 310 and air or the skin with respect to an incident light, each of the light extracting patterns 320 allows light to transmit through the lower surface of the waveguide 310. Since a part of light scattered to the lower surface of the waveguide 310 by the light extracting patterns 320 does not satisfy a total reflection condition (i.e., in a case where an incident angle is smaller than a critical angle), the part of scattered light transmitted through the lower surface of the waveguide 310, and is outputted (radiated) to the outside of the waveguide 310. Also, as both light traveling as it stands without being scattered by the light extracting patterns 320 and the rest of the scattered light satisfy the total reflection condition, the traveling light and the rest of the scattered light continue to travel inside the waveguide 310, and are then incident to different light extracting patterns. Each of the light extracting patterns 320 can be either a scratch, concave-convex, a prism pattern, or other similar light diverting patterns, formed by either printing, photolithography, lasing, and/or stamping. Each of the light extracting patterns 320 can have solid structures with various shapes, such as a cone, a hemisphere, a hexahedron, a triangular pyramid, a quadrangular pyramid, and so forth, and can be formed in a shape of intaglio or an embossed shape on the upper surface of the waveguide 310. Selectively, desired light extracting patterns are applied to a mold, and the waveguide 310 and the light extracting patterns 320 can be simultaneously formed through injection molding using the mold. Each of the light extracting patterns 320 can be provided in a form of Bragg grating, etc., that has a periodic variation of a refractive index, and this kind of variation of a refractive index can be implemented through polling, the irradiation of ultraviolet rays, and the like. The light extracting patterns 320 can be formed on the lower surface of the waveguide 310. In the present embodiment, while the light extracting patterns 320 is limited to scattering an incident light, other than this the light extracting patterns 320 can be provided in a form of a coating layer, etc., that has a refractive index (e.g., a refractive index similar to a refractive index of the waveguide 310) that destroys a total internal reflection condition. In the present embodiment, while multiple light extracting patterns are limited to being formed on the upper surface of the waveguide 310, a single light extracting pattern continuously formed all over the upper surface of the waveguide 310 can exist.

The third light sources 240A are symmetrically arranged with the photo detector 210 as the center, and respective output ends of the third light sources 240A face the outer circumferential surface of the waveguide 310. Each of the third light sources 240A couples a third light having a second wavelength in the band of near infrared rays to the inside of the waveguide 310.

Since light coupled from each of the third light sources 240A to the inside of the waveguide 310 attenuates by degrees while traveling in a circumferential direction of the waveguide 310 in the manner of total reflection, in the waveguide 310, the amount of light that transmits a part nearer to the third light sources 240A can be larger than the amount of light that transmits a part which is more distant from the third light sources 240A. So as to solve these problems, the density or the size of the light extracting patterns 320 in a position nearer to the third light sources 240A is set to be different from the density or the size of the light extracting patterns 320 in a position which is more distant from the third light sources 240A, and with this, an overall distribution of the amount of light that appears on the lower surface of the waveguide 310 can be adjusted, regardless of a distance from the third light sources 240A. For instance, with the third light sources 240A as the reference, the density of light extracting patterns 320 in a relatively near position can be set to be low, and the density of light extracting patterns 320 in a relatively distant position can be set to be progressively higher.

Figure 14:
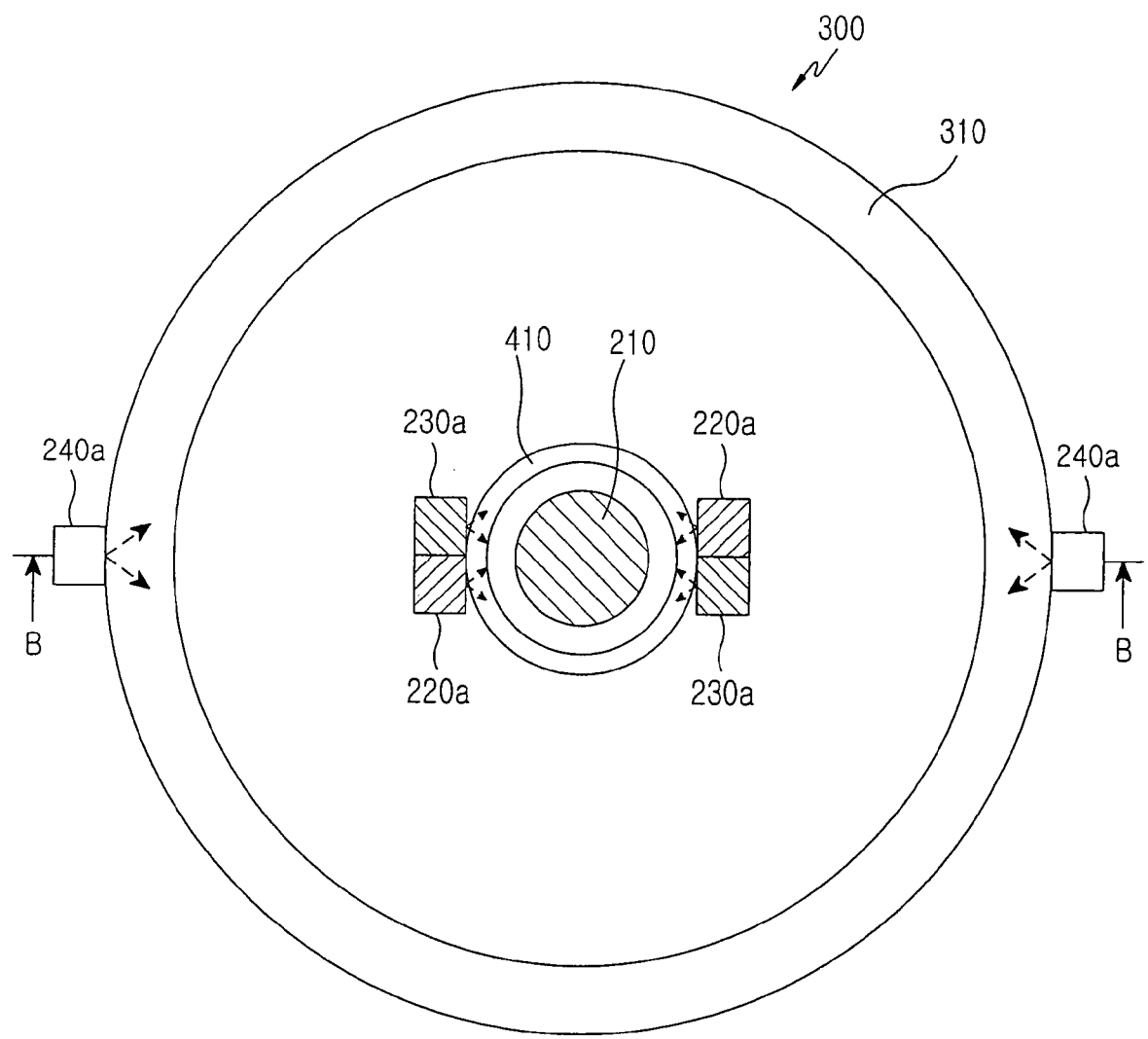
FIG. 14 is a plane view illustrating an apparatus for measuring bio-information according to a third exemplary embodiment of the present invention.
Figure 15:
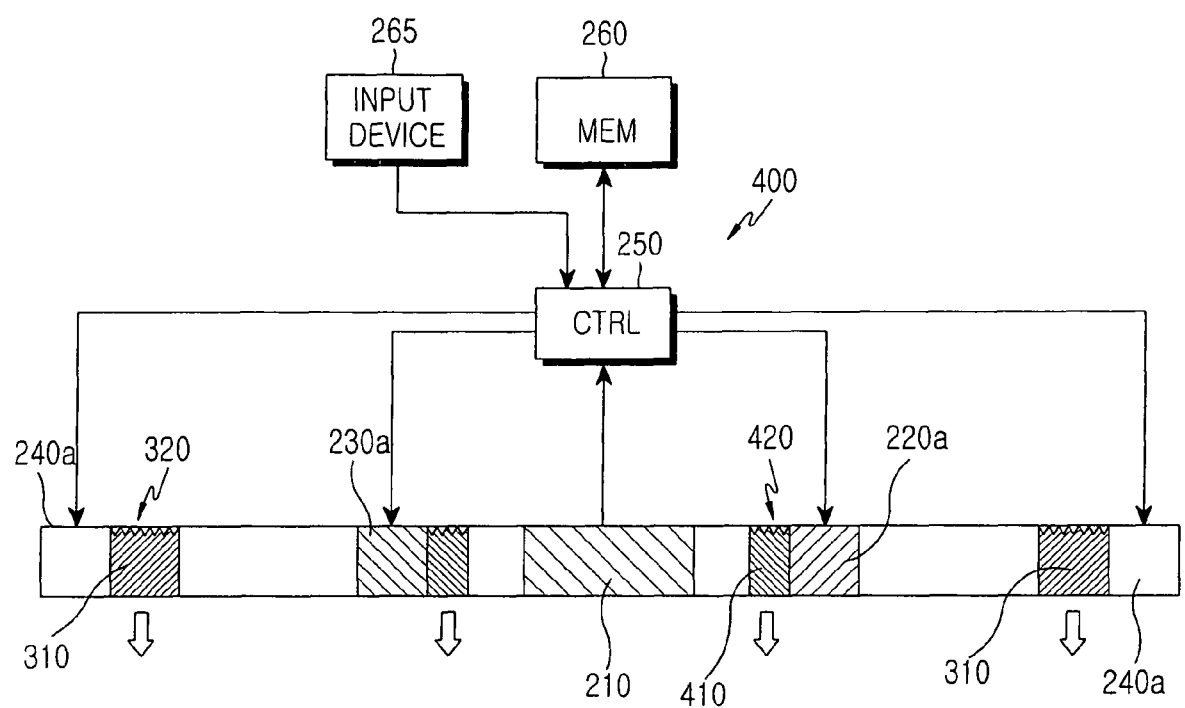
FIG. 15 is a sectional view of the apparatus for measuring bio-information taken along a line B-B in FIG. 14.

FIG. 14 is a plane view illustrating an apparatus for measuring bio-information according to a third exemplary embodiment of the present invention, and FIG. 15 is a sectional view taken along line B-B in the apparatus for measuring bio-information. Since the apparatus 400 for measuring bio-information has a configuration and functions similar to that of the apparatus 300 for measuring bio-information depicted in FIG. 12. The difference between the apparatus 300 and the apparatus 400 is a larger number of first and the second light sources 220A and 230A. This allows for more arrangements corresponding to the increased number of the first and the second light sources 220A and 230A than the apparatus 300. Further, a second waveguide 410 is included. Similar, elements are designated by the same reference numerals, and an overlapping description will be omitted. The apparatus 400 for measuring bio-information includes a photo detector 210, multiple first light sources 220A, multiple second light sources 230A, multiple third light sources 240A, first and the second waveguides 310 and 410, a memory 260, an input device 265, and a controller 250.

The second waveguide 410, having a shape of a circular ring, is arranged on the surface of the skin so as to surround the photo detector 210 and the first and second light sources 220 and 230. The second waveguide 410 has an inner circumferential surface and an outer circumferential surface opposite each other, and has an upper surface and a lower surface opposite each other. The lower surface of the second waveguide 410 functions as an output end, and can be tightly contact with the surface of the skin or can be separate from the skin surface. A sectional surface perpendicular to a circumferential direction (i.e., a direction perpendicular to the direction of a diameter of the second waveguide 410) thereof has a substantially square shape. The second waveguide 410 has a larger refractive index than air or the skin, and light travels in the manner of total reflection in a circumferential direction inside the second waveguide 410. The second waveguide 410 can be implemented by using the same or similar material as that of first waveguide 310.

The upper surface of the second waveguide 410 is equipped with multiple light extracting patterns 420 formed to output light traveling to the inside of the second waveguide 410 to the outside of the second waveguide 410 through the lower surface thereof. Each of the light extracting patterns 420 scatters an incident light. The light extracting patterns 420 are formed symmetrically with the center of curvature of the second waveguide 410 as the reference. By destroying a total internal reflection condition on a boundary surface between the second waveguide 410 and air or the skin with respect to an incident light, each of the light extracting patterns 420 allows light scattered at the light extracting patterns 420 to transmit the lower surface of the second waveguide 410. Since a part of light scattered to the side of the lower surface of the second waveguide 410 by the light extracting patterns 420 does not satisfy a total reflection condition (i.e., in a case where an incident angle is smaller than a critical angle), the part of scattered light transmits through the lower surface of the second waveguide 410, and is thus output outside of the second waveguide 410. Also, as both light traveling as it stands without being scattered by the light extracting patterns 420 and the rest of the scattered light satisfy the total reflection condition, the traveling light and the rest of the scattered light continue to travel inside the second waveguide 410, and are then incident to different light extracting patterns. Each of the light extracting patterns 420 can have the same shape as that of light extracting patterns 320 formed in the first waveguide 310.

The first light sources 220A are symmetrically arranged with the photo detector 210 as the center, and respective output ends of the first light sources 220A face the outer circumferential surface of the second waveguide 410. The second light sources 230A are symmetrically arranged with the photo detector 210 as the center, and respective output ends of the second light sources 230A face the outer circumferential surface of the second waveguide 410. Each of the first light sources 220A couples a first light having a first wavelength to the inside of the second waveguide 410, and each of the second light sources 230A couples a second light having a second wavelength to the inside of the second waveguide 410. In the present embodiment, while a single first light source 220A and a single second light source 230A contact closely with each other to form a pair, with the photo detector 210 as the center, the first light sources 220A are arranged on a first axis, and the second light sources 230A can be arranged on a second axis perpendicular to the first axis.

In the above-described embodiments, while a single photo detector is arranged right in the center of the apparatus for measuring bio-information, and multiple light sources are arranged around the photo detector, a pair of light sources may be arranged in the center of the apparatus, and multiple photo detectors can be arranged around the pair of light sources.

Figure 16:
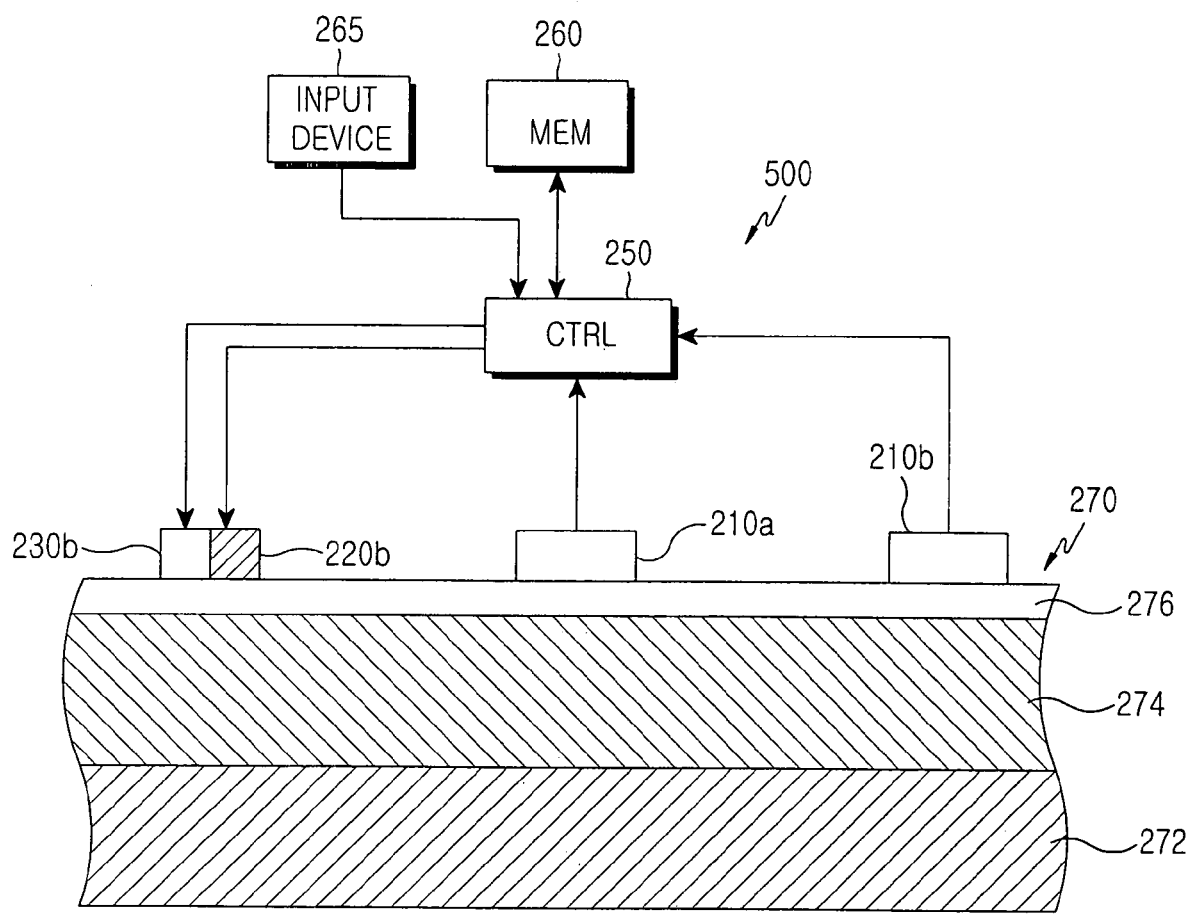
FIG. 16 is a sectional view illustrating an apparatus for measuring bio-information according to a fourth exemplary embodiment of the present invention.

FIG. 16 is a sectional view illustrating an apparatus for measuring bio-information according to a fourth exemplary embodiment of the present invention.

The apparatus for measuring bio-information 500 has a configuration and function similar to that of apparatus 200 depicted in FIG. 3. The, difference between the apparatus 200 and the apparatus 500 in the arrangements and the number of photo detectors 210A and 210B and the arrangement and the number of first and second light sources 220B and 230B. Therefore, similar elements shown in FIGS. 3 and 12 will be designated by the same reference numerals, and an overlapping description will be omitted.

Biological tissue 270 has a structure in which respective layers corresponding to muscle 272, subcutaneous fat 274, and skin 276 are laminated in that order. The apparatus 200 for measuring bio-information includes a first light source 220B, a second light source 230B, a first photo detector 210A, a second photo detector 210B, a Memory (MEM) 260, an input device 265, and a Controller (CTRL) 250.

The first light source 220B is arranged on the surface of the skin 276, and radiates a first light having a first wavelength (e.g., 660 nm) in the band of visible light on the surface of the skin 276.

The second light source 230B is arranged on the surface of the skin 276 so as to be in close contact with the first light source 220B, and radiates a second light having a second wavelength (e.g., 880 nm) in the band of near infrared rays on the surface of the skin 276.

The first photo detector 210A is arranged on the surface of the skin 276 so as to be separate from the first and the second light sources 220B and 230B, and outputs an electrical signal which has been converted by photoelectric conversion from an input light The second photo detector 210B is arranged on the surface of the skin 276 in such a manner as to be placed in a more distant position from the first and the second light sources 220B and 230B than the first photo detector 210A, and outputs an electrical signal from an input light In the present embodiment, a distance between the first photo detector 210A and the first and second light sources 220B and 230B equals 2 mm, and a distance between the second photo detector 210B and the first and second light sources 220B and 230B equals 10 mm. Desirably, a distance between the first photo detector 210A and the first and second light sources 220B and 230B is equal to or shorter than 5 mm, and a distance between the second photo detector 210B and the first and second light sources 220B and 230B is equal to or longer than 10 mm.

A light received by the first photo detector 210A among rays of the first light is specifically referred to as a "first detection light", a light received by the first photo detector 210A among rays of the second light is specifically referred to as a "second detection light", and a light received by the second photo detector 210B among rays of the second light is specifically referred to as a "third detection light."

The memory 260 stores a table required to express relations between the basic bio-information and the second coefficients necessary to compute the basic bio-information and the thickness of subcutaneous fat.

The controller 250 enables the first and the second light sources 220B and 230B to be driven one by one, computes the color of the skin 276 on the basis of the intensities of the first and the second detection lights sequentially detected by the first photo detector 210A, and computes skin color (i.e., an MI) and the thickness of subcutaneous fat 274 on the basis of the intensity of the third detection light detected by the second photo detector 210B and the table. To this end, the controller 250 is electrically connected with the first and second light sources 220B and 230B and the first and second photo detectors 210A and 210B, receives output signals from the first and the second photo detectors 210A and 210B, and outputs a driving signal to each of the first and the second light sources 220B and 230B.

In the fourth embodiment of the present invention, while it is exemplified that the first and the second light sources which output lights having wavelengths different from each other are used, lights having wavelengths different from each other can be simultaneously output, or a single light source whose wavelength is variable can be used.

Also, in the embodiments of the present invention, while it is exemplified that only the color of the skin and the thickness of subcutaneous fat are measured, various pieces of bio-information can be derived by using the first to the third detection lights. For example, because a wavelength of near infrared rays is used, a pulse wave is measured at the tip of the finger in which capillary vessels aggregate densely, and then, heart rate variability (in other words, stress) can be derived. In addition, since a wavelength of near infrared rays and a wavelength of visible light are used simultaneously, oxygen saturation changes in the blood (i.e., percent $SPO_2$) can also be measured. Besides, a waveform of changes of blood flow volume of a peripheral artery (i.e., PhotoPlenthysmoGraphy; PPG), breathing rate per minute, pulse, and the like can also be measured.

The merits and effects of exemplary embodiments, as disclosed in the present invention, and as so configured to operate above, will be described as follows.

As described above, an apparatus for measuring bio-information according to the present invention is different from the prior apparatus for measuring bio-information, in that it not only considers the influence of the skin the prior apparatus for measuring bio-information, but also receives basic biological information from a user, thereby providing a more accurate measurement of the thickness of subcutaneous fat by reflecting the received basic biological information.

Furthermore, in the apparatus for measuring bio-information according to the present invention, since a fewer number of light sources can be employed by using a waveguide than in the prior apparatus, it is suitable for a mobile terminal requiring a high economic efficiency.

The above-described controller according to the present invention can be realized in hardware or as software or computer code that can be stored in a recording medium such as a CD ROM, an RAM, a floppy disk, a hard disk, or a magneto-optical disk or downloaded over a network, so that the methods described herein can be rendered in such software using a general purpose computer, or a special processor or in programmable or dedicated hardware, such as an ASIC or FPGA. As would be understood in the art, the computer, the processor or the programmable hardware include memory components, e.g., RAM, ROM, Flash, etc. that may store or receive software or computer code that when accessed and executed by the computer, processor or hardware implement the processing methods described herein.

While the invention has been shown and described with reference to certain exemplary embodiments thereof, it will be understood by those skilled in the art that various changes in form and details may be made therein without departing from the spirit and scope of the invention. Therefore, the spirit and scope of the present invention must be defined not by described embodiments thereof but by the appended claims and equivalents of the appended claims.

What is claimed is:

1. An apparatus for measuring bio-information of a user, the apparatus comprising:
    a device for receiving, from the user, basic bio-information including height and weight of the user;
    a first light source for radiating a first light having a first wavelength toward a surface of the user's skin;
    a second light source for radiating a second light having a second wavelength toward the surface;
    a third light source for radiating a third light having a third wavelength toward the surface;
    a photo detector detecting a first, a second and a third detection light which are transmitted through the surface and generating corresponding electrical signals, said first, second and third detection light corresponding to said light radiating from said first, second and third light sources, respectively, wherein said first and second light sources are alternatively arranged around said photo detector and said third light source is separately positioned more distant from the photo detector than the first and the second light sources; and
    a control unit for enabling the first to the third light sources to be driven in a known order and for producing bio-information of the user on the basis of the basic bio-information and intensities of the first to the third detection lights, wherein said first and second light sources are separated from said photo detector by no more than 5 millimeters and the third light source is separated from said photo detector by no less than 10 millimeters.

2. The apparatus as claimed in claim 1, wherein the control unit produces a Melanin Index (MI) as:

$MI = A + B \ln(I_1/I_2)$, where A and B represent preset coefficients,
$I_1$ represents the intensity of the first detection light,
$I_2$ represents the intensity of the second detection light, and
ln represents the natural logarithmic function.

3. The apparatus as claimed in claim 1, wherein the control unit computes the thickness of subcutaneous fat as:

$SAT_P = C_P + D_P BMI + E_P I_{MI}$, $I_{MI} = I_3/(I_1/I_2)$, and $BMI = WT/HT^2$, where $SAT_P$ represents the thickness of subcutaneous fat,
$C_P$, $D_P$ and $E_P$ represent preset coefficients,
$I_1$ represents the intensity of the first detection light,
$I_2$ represents the intensity of the second detection light,
$I_3$ represents the intensity of the third detection light,
WT represents the weight of the user, and
HT represents the height of the user.

4. The apparatus of claim 3, further comprising:
a memory for storing a table required to express relations between the basic bio-information and coefficients necessary to compute a thickness of subcutaneous fat.

5. The apparatus as claimed in claim 1, wherein the control unit computes the percent body fat as:

$PBF_P = F_P + G_P BMI + H_P AGE + I_P I_{MI}$, $I_{MI} = I_3/(I_1/I_2)$, and $BMI = WT/HT^2$, where $PBF_P$ represents the percent body fat,
$F_P$, $G_P$, $H_P$ and $I_P$ represent preset coefficients,
$I_1$ represents the intensity of the first detection light,
$I_2$ represents the intensity of the second detection light,
$I_3$ represents the intensity of the third detection light,
WT represents the weight of the user,
HT represents the height of the user, and AGE represents an age of the user.

6. The apparatus as claimed in claim 5, further comprising:
a memory for storing a table required to express relations between the basic bio-information and coefficients necessary to compute a percent body fat.

7. The apparatus as claimed in claim 1, wherein the first wavelength belongs to a band of visible light, and the second and the third wavelengths belong to a band of near infrared rays.

8. The apparatus as claimed in claim 1, further comprising:
a waveguide positioned between the first and second light sources and the third light source, enabling the third light provided from the third light source to travel by total reflection within said waveguide; and
at least one light extracting pattern for directing the third light outside of the waveguide.

9. The apparatus as claimed in claim 8, wherein the waveguide has a shape of a circular ring, and is equipped with a lower surface facing the surface and an upper surface opposite the lower surface, and the light extracting pattern is formed on the upper surface of the waveguide.

10. The apparatus as claimed in claim 1, further comprising:
a waveguide positioned between the photo detector and the first and second light sources, enabling the first or the second light provided from the first or the second light source to travel by total reflection within the waveguide; and
at least one light extracting pattern for directing the first or the second light outside the waveguide.

11. The apparatus as claimed in claim 10, wherein the waveguide has a shape of a circular ring, and is equipped with a lower surface facing the surface and an upper surface opposite the lower surface, and the light extracting pattern is formed on the upper surface of the waveguide.

12. The apparatus as claimed in claim 1, wherein the second and the third wavelengths are substantially the same.

13. The apparatus as claimed in claim 12, wherein the first wavelength is different from the second and third wavelengths, the first wavelength is in a range of 600 nm to 750 nm and each of the second and third wavelengths is in a range of 750 nm to 1000 nm.

* * * * *